(12) United States Patent
Gliklich et al.

(10) Patent No.: US 8,128,618 B2
(45) Date of Patent: Mar. 6, 2012

(54) TARGETED MUSCLE ABLATION FOR REDUCING SIGNS OF AGING

(75) Inventors: Richard E. Gliklich, Weston, MA (US); William Matthew White, South Boston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 587 days.

(21) Appl. No.: 11/462,191

(22) Filed: Aug. 3, 2006

(65) Prior Publication Data
US 2007/0032784 A1 Feb. 8, 2007

Related U.S. Application Data

(60) Provisional application No. 60/705,030, filed on Aug. 3, 2005.

(51) Int. Cl.
*A61B 18/04* (2006.01)
(52) U.S. Cl. .................................. 606/27; 606/32
(58) Field of Classification Search ............... 606/27–32
See application file for complete search history.

(56) References Cited

U.S. PATENT DOCUMENTS

| | | | |
|---|---|---|---|
| 4,979,501 A | 12/1990 | Valchanov et al. | |
| 5,012,797 A | 5/1991 | Liang et al. | |
| 5,143,074 A | 9/1992 | Dory | |
| 5,458,596 A | 10/1995 | Lax et al. | |
| 5,520,188 A | 5/1996 | Hennige et al. | |
| 5,558,092 A | 9/1996 | Unger et al. | |
| 6,113,559 A | 9/2000 | Klopotek | |
| 6,277,116 B1 | 8/2001 | Utely et al. | |
| 6,361,806 B1 * | 3/2002 | Allen | 424/740 |
| 6,430,446 B1 | 8/2002 | Knowlton | |
| 6,438,424 B1 | 8/2002 | Knowlton | |
| 6,440,121 B1 | 8/2002 | Weber et al. | |
| 6,461,378 B1 | 10/2002 | Knowlton | |
| 6,470,216 B1 | 10/2002 | Knowlton | |
| 6,595,934 B1 | 7/2003 | Hissong et al. | |
| 6,623,430 B1 | 9/2003 | Slayton et al. | |
| 6,936,046 B2 * | 8/2005 | Hissong et al. | 606/27 |
| 2001/0025190 A1 | 9/2001 | Weber | |
| 2003/0212351 A1 * | 11/2003 | Hissong et al. | 601/2 |
| 2004/0138555 A1 * | 7/2004 | Krag et al. | 600/424 |
| 2004/0206365 A1 * | 10/2004 | Knowlton | 128/898 |
| 2004/0210214 A1 | 10/2004 | Knowlton | |
| 2005/0055073 A1 | 3/2005 | Weber | |
| 2005/0267454 A1 * | 12/2005 | Hissong et al. | 606/27 |

(Continued)

FOREIGN PATENT DOCUMENTS

DE 10219297 11/2003

(Continued)

OTHER PUBLICATIONS

Letter from Ulthera, Inc. representative dated Aug. 27, 2007 and accompanying Appendices A and C (10 pages).

(Continued)

*Primary Examiner* — Linda Dvorak
*Assistant Examiner* — Amanda Scott
(74) *Attorney, Agent, or Firm* — Fish & Richardson P.C.

(57) ABSTRACT

A method and system for delivering energy to affect the signs of aging is described. Energy is delivered to a target volume of a muscle such that the energy creates a lesion in the target volume. A characteristic of the lesion is controlled to affect movement of the muscle.

12 Claims, 5 Drawing Sheets

U.S. PATENT DOCUMENTS

| | | | |
|---|---|---|---|
| 2006/0058664 A1 | 3/2006 | Barthe et al. | |
| 2006/0074355 A1 | 4/2006 | Slayton et al. | |
| 2006/0116671 A1 | 6/2006 | Slayton et al. | |
| 2006/0122508 A1* | 6/2006 | Slayton et al. | 600/439 |
| 2007/0032784 A1 | 2/2007 | Gliklich et al. | |
| 2007/0255355 A1* | 11/2007 | Altshuler et al. | 607/86 |

FOREIGN PATENT DOCUMENTS

| | | |
|---|---|---|
| GB | 2113099 | 8/1983 |

OTHER PUBLICATIONS

Letter from Ulthera, Inc. representative dated Jan. 2, 2008 and accompanying Appendices A and B (8 pages).

Exhibit D of Letter from Ulthera, Inc. representative dated Aug. 27, 2007 (18 pages).

Exhibit C of Letter from Ulthera, Inc. representative dated Jan. 2, 2008 (11 pages).

International Preliminary Report on Patentability for Application No. PCT/US2006/030553 dated Feb. 14, 2008.

Kennedy et al., "High Intensity Focused Ultrasound: Surgery of the Future?", Brit. J. Radiol., vol. 76, pp. 590-599 (2003).

Meaney et al., "The Intensity Dependence of Lesion Position Shift During Focused Ultrasound Surgery", Ultrasound in Med. & Biol., vol. 26(3), pp. 441-450 (2000).

Seip et al., "Transurethreal high Intensity Focused Ultrasound: Catheter based Prototypes and Experimental Results", 2000 IEEE Ultrasonics Symposium, pp. 1413-1416 (2000).

Watkin et al., "The Intensity Dependence of the Site of Maximal Energy Deposition in Focused Ultrasound Surgery", Ultrasound in Med. & Biol., vol. 22(4), pp. 483-491 (1996).

International Search Report in Application No. PCT/US2005/034358, dated Dec. 23, 2005, 9 pgs.

Office Action of Mar. 14, 2007, Form 1449s, Form 892s from U.S. Appl. No. 10/950,112 (Slayton et al.), 29 pgs.

International Preliminary Report on Patentability in Application No. PCT/US2005/036377, dated Jan. 1, 2007, 6 pgs.

International Search Report in Application No. PCT/US2005/036377, dated Jan. 24, 2006, 4 pgs.

Form 1449s from U.S. Appl. No. 11/163,151 (Slayton et al.), 2 pgs., (2007).

International Preliminary Report on Patentability in Application No. PCT/US2005/036269, dated Jan. 19, 2007, 7 pgs.

International Search Report in Application No. PCT/US2005/036269, dated Jan. 26, 2006, 4 pgs.

Form 1449s from U.S. Appl. No. 11/163,148 (Slayton et al.), 11 pgs., (2009).

International Search Report in Application No. PCT/US2005/033195, dated Jan. 26, 2006, 4 pgs.

International Preliminary Report on Patentability in Application No. PCT/US2005/033195, dated Dec. 22, 2006, 7 pgs.

Form 1449s from U.S. Appl. No. 10/944,500 (Barthe et al.), 19 pgs., (2009).

Office Action of Feb. 12, 2007 in U.S. Appl. No. 10/944,500 (Barthe et al.), 26 pgs.

International Search Report for Application No. PCT/US2006/30553, (dated Jul. 10, 2007).

Written Opinion for Application No. PCT/US2006/30553, (dated Jul. 10, 2007).

* cited by examiner

FIG. 5

TARGETED MUSCLE ABLATION FOR REDUCING SIGNS OF AGING

CROSS-RELATED APPLICATION

Under 35 U.S.C. 119(e)(1), this application claims the benefit of provision application Ser. No. 60/705,030, filed Aug. 3, 2005, and entitled, "Transcutaneous Delivery of Ultrasound for Reducing Signs of Aging."

TECHNICAL FIELD

This invention relates to medical applications of ultrasound, and more particularly to using ultrasound to reduce wrinkles and sagging skin.

BACKGROUND

As a person ages, the skin, underlying connective tissue, and muscle undergo changes that result in wrinkles and sagging skin. These changes occur all over the body but are often most noticeable in the face.

Current methods for reducing wrinkles and tightening sagging skin include surgical procedures, such as rhytidectomy (i.e., a face lift), brow lifts, and blepharoplasty (i.e., eyelid surgery), botulinum toxin injection, and skin resurfacing techniques (e.g., chemical peels).

Surgical procedures for tightening sagging skin usually involve making an incision in the skin and underlying layers, elevating the skin and soft tissue, and stretching the underlying muscle and membrane layers to a desired level of tightness. The amount by which sagging skin may be tightened is often limited by the underlying elasticity of the muscle and membrane layers and the degree to which these layers relax after surgery.

Surgical procedures for reducing wrinkles involve selectively destroying muscles, or parts of muscles that primarily contribute to the formation of wrinkles. Selective muscle destruction may be performed openly or endoscopically; however, both techniques require direct visualization of the muscle groups and employ invasive procedures, such as avulsion, incision, and direct cautery for removing portions of muscle. Because of their invasive nature, surgical procedures often require prolonged recovery time, and put patients at risk for potential complications, such as hematoma.

Botulinum toxin injection reduces wrinkles by temporarily paralyzing muscles whose movement causes skin to wrinkle. Patients may have variable responses to an injection of the same dosage depending on patient factors that are not determinable prior to injection. Because the effects of an injection are temporary, repeated injections are typically needed every four to six months to maintain a desired result. Furthermore, when the toxin is applied to the forehead and brow, the resulting muscle paralysis may cause brow ptosis and/or a noticeable loss of facial animation.

Skin resurfacing techniques include delivery of energy to layers of the skin including the epidermis and dermis using lasers, chemical agents, and radiofrequency delivery devices. These techniques often have limited penetration depth and therefore are limited to treating superficial layers of the skin. Some skin resurfacing techniques may cause uneven pigmentation in the skin. Although these techniques may improve the texture of the skin, they often do little to tighten sagging skin and to reduce wrinkles.

SUMMARY

The invention provides methods and systems for reducing signs of aging.

In one aspect, the invention features a method that includes producing a map of a muscle; locating a target volume of the muscle using the map; and delivering energy to the target volume such that the energy creates a lesion in the target volume, the lesion having a characteristic selected for affecting movement of the muscle.

In another aspect, the invention features a method that includes producing a map of SMAS tissue; locate a target volume of the SMAS tissue using the map; and delivering energy to the target volume such that the energy creates a lesion in the target volume, the lesion having a characteristic selected for affecting movement of the SMAS tissue.

In a further aspect, the invention features a method that includes producing a map of target tissue including muscle and SMAS tissue; locating a target volume of the target tissue using the map; delivering energy to the target volume such that the energy creates a pattern of lesions in the target volume; and selecting the pattern to impact the degree and direction of movement of the target tissue.

In another aspect, the invention features a system that includes an ablating transducer configured to deliver ablative radiation (e.g., ultrasound) at a power sufficient to ablate muscle tissue; and control circuitry in communication with the ablating transducer. The control circuitry is configured to receive lesion pattern specifications (e.g., size and depth specifications of the lesions of a pattern) and stimulate the ablating transducer to produce a pattern of lesions within the target volume. The pattern is produced in accordance with the lesion pattern specifications and selected to impact a degree of paralysis of a muscle.

Embodiments may include one or more of the following. The characteristic may be one of a size, a shape, an orientation, a depth below an epidermal surface, and a location relative to another lesion. The characteristic may be selected to reduce movement of the muscle and/or produce a contraction of the muscle. The characteristic may be selected to induce contraction of the SMAS tissue in a desired direction. For example, the characteristic may be selected to release the SMAS tissue from muscle tissue causing skin attached to the SMAS tissue to be pulled in a desired direction.

The pattern of lesions may be selected to impact the degree and direction of movement of SMAS tissue. For examples, the pattern of lesions may be one of: a square, triangle, polygon, grid, criss-cross pattern, circle, oval, and coil. The pattern may also be a matrix of lesions (e.g., each approximately 1mm$^3$ in volume) spaced approximately equidistant from each other (e.g., such that the spacings between the lesions are approximately 1 mm). The density of the lesions of the pattern may be selected to achieve a desired degree of contraction of the SMAS tissue within the target volume. Furthermore, the spacings between the lesions of a pattern may be selected to achieve a desired degree of paralysis of the muscle tissue within the target volume.

The delivered energy may be ultrasound or radio frequency electromagnetic energy. For example, the energy may be ultrasound having a frequency within a range of 4 to 8 MHz and a power within a range of 60 to 80W. A map of a target tissue may be obtained by acquiring an echo image from echoes generated by reflections of ultrasound pulses directed towards the target tissue.

The imaging transducer may be configured to deliver ultrasound radiation at a power sufficient to produce an echo image of a target volume of tissue without damaging tissue within the target volume.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims, in which

DETAILED DESCRIPTION

Figure 1:
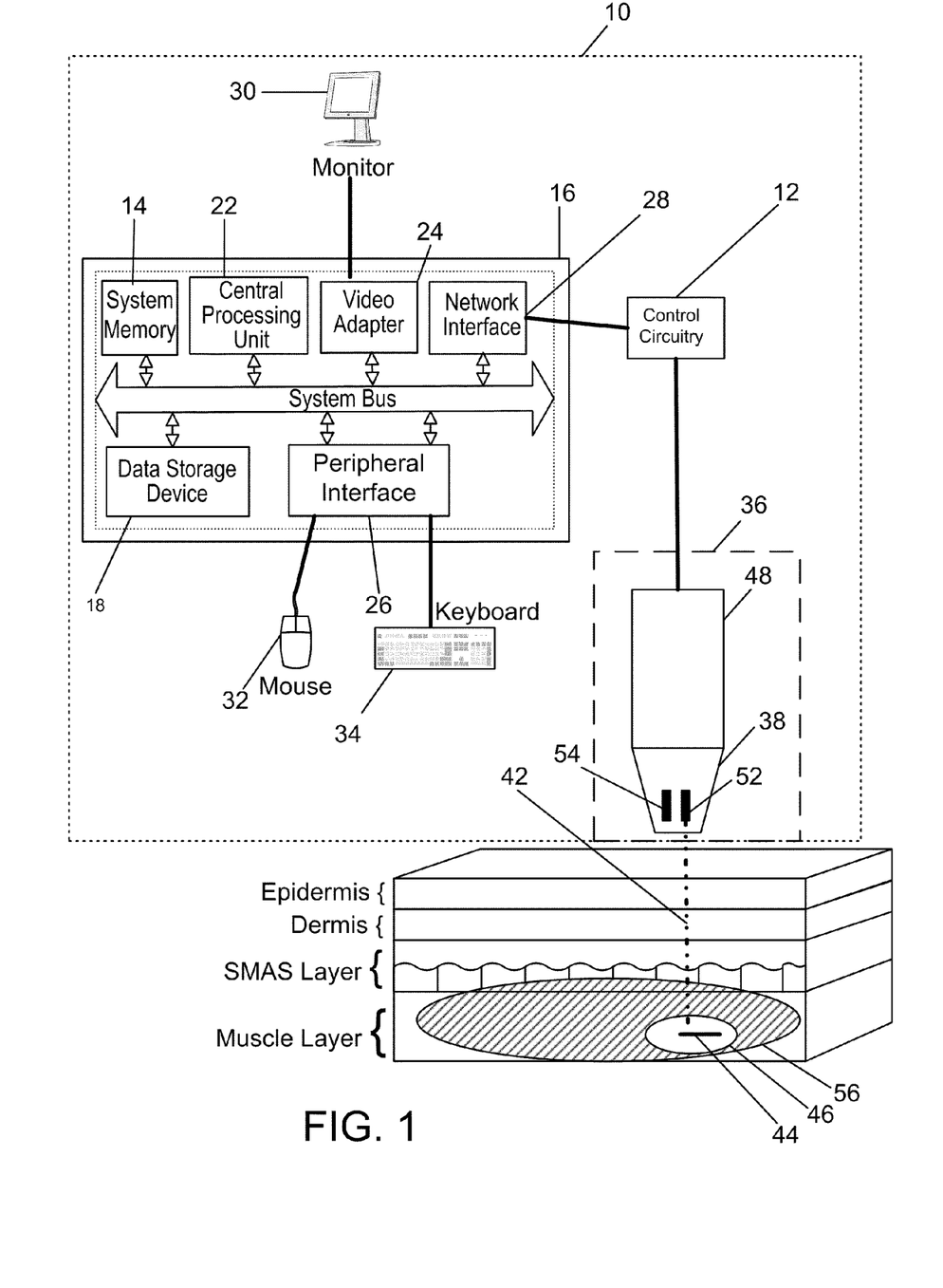
FIG. 1 shows a block diagram of a system for ablating tissue using ultrasound.

FIG. 1 shows a block diagram of an ultrasound delivery system 10 for ablating a target volume 44 of muscle tissue within a muscle 56. In some embodiments, the muscle 56 is located in the face. Examples of the muscle 56 include the corrugator, procerus, and frontalis muscles of the brow and forehead. The muscle 56 is located beneath a connective tissue layer called the superficial musculo-aponeurotic system (SMAS) layer. The SMAS layer envelopes underlying muscles (e.g., platysma muscle in the neck and frontalis muscle in the forehead), including the muscle 56, and is tethered to the overlying dermis and epidermis layers of the skin. The SMAS layer includes a portion of muscle 56. When the muscle 56 contracts, the resultant pull of the SMAS layer on the skin produces visible facial expressions and causes the skin to wrinkle. Repeated contraction of the muscle 56 produces wrinkles in the skin. Over time, gravity causes the SMAS layer to loosen and this leads to more pronounced wrinkles and sagging skin. In some embodiments, ultrasound delivery system 10 ablates a target volume 44 of connective tissue located within the SMAS layer, rather than a target volume 44 of muscle 56, causing the SMAS tissue to contract in a desired direction.

The ultrasound delivery system 10 includes an ultrasound applicator 36 for imaging the muscle 56 and for delivering ablating ultrasound radiation 42 ("ablating radiation") to the target volume 44. The ablating radiation 42 heats the tissue in the target volume 44 until a finite volume of that tissue coagulates and forms a lesion 46. The ultrasound delivery system 10 also includes control circuitry 12 for controlling the ablating radiation 42 emitted from the ultrasound applicator 36, a computer 16 that transmits control commands to and receives data from the ultrasound applicator 36 via the control circuitry 12, a monitor 30 for displaying images of the muscle 56, and a mouse 32 and keyboard 34 for entering commands into the computer 16.

The computer 16 includes a data storage device 18, such as a hard drive, for storing images of the muscle 56, system memory 14, such as random-access memory (RAM), for loading software programs that perform image processing and ablation control functions, and a central processing unit 22 for executing software instructions stored in the system memory 14. The computer 16 also includes a video adapter 24 that interfaces the monitor 30, a peripheral control interface 26 for receiving signals from the mouse 32 and the keyboard 34, and a network interface 28 for transmitting signals between the computer 16 and the control circuitry 12. In some embodiments the network interface 28 is a serial port, a parallel port, a universal-bus (USB) interface, or a peripheral component interface (PCI). In other embodiments, the control circuitry 12 is integrated within the computer 16.

The ultrasound applicator 36 includes a handle 48 and a probe tip 38 that is removably attached to the applicator handle 48. The probe tip 38 includes an ablating transducer 52 and an imaging transducer 54. The ablating transducer 52 emits high-power ultrasound radiation (i.e., ablating radiation 42) for ablating muscle tissue. The imaging transducer 54 emits low-power ultrasound radiation (hereinafter referred to as "imaging radiation") for producing an echo image of the muscle 56 without damaging any tissue. The imaging transducer 54 detects the echoes of the imaging radiation after it bounces off the muscle 56. During ablation, the control circuitry 12 receives a control signal from the computer 16 and produces an electrical signal as a response. The electrical signal in turn stimulates the ablating transducer 52 to produce ablating radiation 42. The ablating radiation 42 is then emitted from the probe tip 38 with a fixed frequency and power. In some embodiments, the applicator 36 is configured to lay down a pattern of multiple lesions simultaneously or sequentially. An example of such a pattern is a line of five 1 mm$^3$ lesions spaced 1 mm apart from each other.

The probe tip 38 is selected from a set of interchangeable probe tips having different frequency and power output specifications. The frequency of the ablative radiation 42 limits how deep within the tissue a lesion 46 can be formed; and the power of the ablative radiation 42 affects the size of the lesion 46. The frequency and power output specifications of the probe tip 38 are selected to produce a lesion 46 of a determined size and depth. If the size and depth specifications of the lesion 46 change such that the frequency and power specifications of the probe tip 38 are no longer sufficient to produce lesions with the new size and depth specifications, the probe tip 38 is replaced with another probe tip 38 that has sufficient power and frequency specifications. In some embodiments, some of the interchangeable probe tips produce different patterns of lesions. Examples of lesion patterns include squares, triangles, polygons, grids, and criss-cross patterns. Examples of grid patterns (also referred to as "matrix patterns") include a two- or three-dimensional grid of approximately equally spaced lesions in which the spacings between lesions is approximately equal to a dimension of the lesion. In one such grid pattern, the volumes of the lesions are approximately 1 mm$^3$ and the spacings between lesions are approximately 1 mm. In another grid pattern the spacings between lesions are approximately 1.5 to 2.0 mm. In further grid patterns the volumes of lesions may be greater than or less than 1 mm$^3$ and the spacings between the lesions may be greater than or less than 1 mm. The pattern specifications (e.g., lesion sizes and spacings) are selected such that distinct lesions separated by a sufficient amount of living tissue can be produced. The patterns of lesions affect the degree to which the movement and tone of the muscle 56 is reduced.

In other embodiments, the applicator 36 is used only for ablating tissue, and a separate imaging device (not shown) is provided for imaging the muscle 56. In these embodiments, the separate imaging device, rather than the applicator 36, includes an imaging transducer 54. In further embodiments, the power and frequency of the ultrasound radiation produced by the ablating transducer 52 may be electronically adjusted by varying the electrical signal produced by the control circuitry 12. Thereby enabling ablating transducer 52 to alternately transmit ablating radiation 42 and imaging radiation. Furthermore, if a lesion pattern is specified at the computer 16, the computer 16 sends the lesion pattern specifications to the control circuitry 12, which in turn stimulates the transducers in the applicator 36 to direct the ablating radiation 42 such that the specified pattern of lesions is produced. In these embodiments, the probe tip 38 need not be interchanged with other probe tips when the frequency, power output, and/or pattern specifications change.

Figure 2:
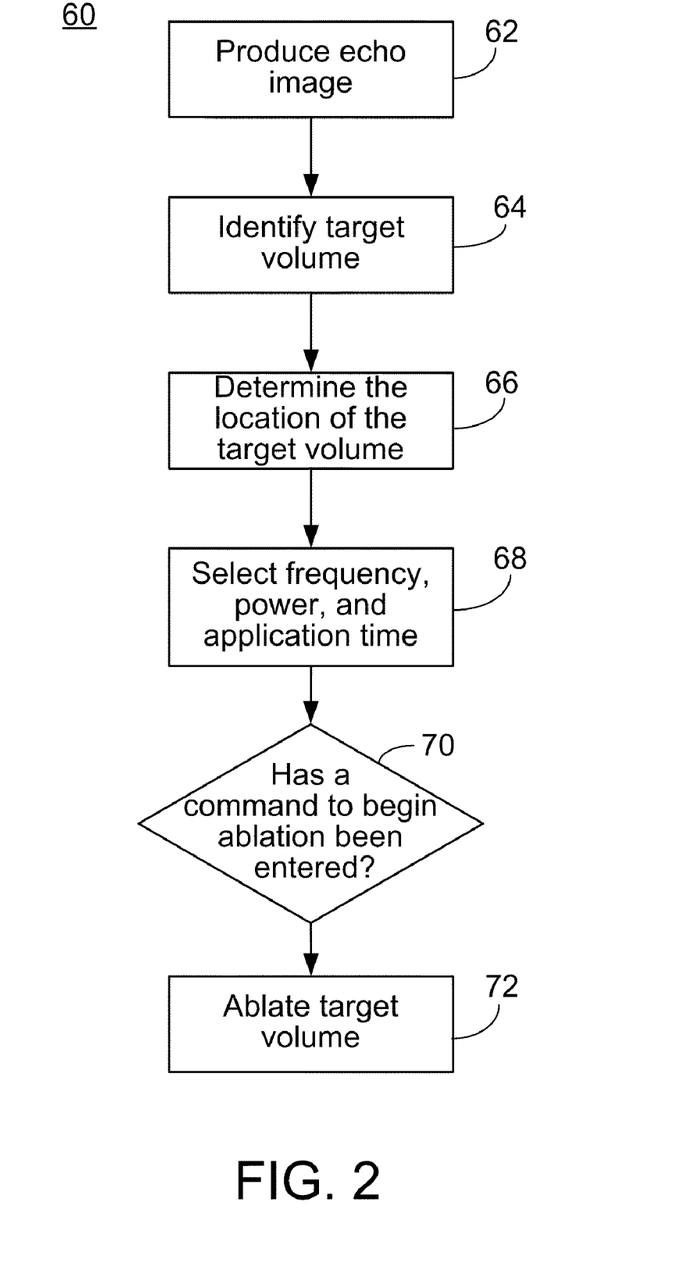
FIG. 2 is a flow chart of a process for ablating tissue using the system shown in FIG. 1.

FIG. 2 shows a process 60 for ablating muscle tissue using the ultrasound delivery system 10. An operator places the ultrasound applicator 36 in direct contact with the epidermis of the patient and positions the applicator 36 above the muscle 56. For example, if the muscle 56 is the corrugator muscle, the applicator 36 is placed in contact with the patient's forehead. An echo image of the muscle 56 is produced using ultrasound echo imaging (step 62). During imaging, the applicator 36 directs imaging radiation (e.g., ultrasound pulses) to the muscle 56 at a power level that avoids damage to tissue. The muscle 56 reflects these pulses, thereby causing echoes. The imaging transducer 54 receives the echoes and translates them into an electrical signal. The applicator 36 then sends this signal to the computer 16 for analysis. The central processing unit 22 analyzes the echo data carried by the signal, constructs an echo image of the muscle 56, and displays that echo image on the monitor 30. From the echo image, the operator identifies a target volume 44 in which to produce a lesion 46 (step 64). The operator also identifies tissue surrounding the target volume 44, such as nerves, that the ablating radiation 42 should avoid. The echo image includes a marker that represents the coordinates of the tissue being viewed in the image. The operator determines the location of the target volume 44 shown in the image by placing the marker over or near the image of the target volume 44 (step 66). Based on the coordinates of the target volume 44, the operator determines the depth of the target volume 44 below the surface of the skin. This depth may vary depending on the thickness of the tissue and where it is located. For facial treatments, the target volume 44 is between approximately 2 mm and 12 mm below the surface of the skin. In some embodiments, a target volume 44 of muscle tissue in the forehead is between approximately 8 mm and 10 mm below the epidermal surface and a target volume 44 of muscle tissue around the eyes is between approximately (2 mm and 5 mm, although variable from person to person) below the epidermal surface. In other embodiments, such as for suspensory ligaments, muscle insertions, periosteal areas and others, the target volume 44 is as much as 2 cm below the epidermal surface.

The extent to which ultrasound radiation 42 can penetrate below the epidermal surface and still retain just enough power to ablate tissue (referred to as penetration depth) depends in part on the frequency of the ablative radiation 42. Lower-frequency ultrasound generally penetrates more deeply than higher-frequency ultrasound. In some embodiments, higher frequency (e.g. 10 MHz) ultrasound is used for dermal treatment and lower frequency ultrasound (e.g. 4-8 MHz) is used for treating layers beneath the dermal layer. The frequency of the ultrasound is selected such that the penetration depth is greater than or equal to the depth of the target volume 44 below the epidermal surface.

In addition to the power, how long one ablates the target volume 44 affects the size of the lesion 46 produced within the target volume 44. The probe tip 38 applies ablative radiation 42 as a series of pulses. The duration of each pulse in a series of applied pulses is referred to as "application time" and the time between pulses is referred to as "off time." In some embodiments, the off time is selected to be between 150 and 200 ms to provide the target tissue sufficient time to cool between each pulse. Increasing the power and/or the application time increases the volume of the lesion 46. The tissue density of the target volume 44 also affects how much power and application time is needed to produce a lesion 46 of a desired volume. In general, higher power and longer application times are needed to produce a lesion 46 of a given volume in denser tissues.

The power output, frequency, and application time of the ultrasound radiation 42 are selected based the depth of the target volume 44 below the epidermal surface and on the density of the tissue within it (step 68). In some embodiments, lesions between approximately 1 mm$^3$ and 5 mm$^3$ are produced by setting the frequency within a range of 4 to 8 MHz, the power within a range of 10 to 100 W, and the application time within a range of 5 to 1000 ms. In some embodiments, the power of the ablative radiation 42 is selected to be within a range of 60 to 80 W. When producing a grid pattern of lesions, the power, frequency, and application time of the ablative radiation 42 are selected to form distinct, non-overlapping, and non-contiguous lesions.

The power output, frequency, and application time may be determined from data acquired in human cadaver, animal, and clinical studies. Examples of a human cadaver and animal studies are described below in the Examples section. The data from various studies may be used to produce a table that stores optimal frequency, power, and application time settings for producing different combinations of lesion depths and volumes for various target muscles (e.g., corrugator and frontalis muscles). In some embodiments, a mathematical model, rather than a table, is used to determine an optimal set of frequency, power, and application time specifications given input values of lesion depth and volume for a given target muscle. The mathematical model may be based wholly or in part on human cadaver, animal, and clinical studies.

The operator selects a probe tip 38 that meets the selected frequency and power output specifications and that can produce lesions arranged in the selected pattern. Examples of three probe tips (P1, P2, and P3) and their specifications are shown below in Table 1.

TABLE 1

| Probe tip | Frequency | Focus | Power | Application time | Total Energy |
|---|---|---|---|---|---|
| P1 | 7.5 MHz | 3.0 mm | 25-40 W | 25-50 ms | 0.5-1.2 J |
| P2 | 7.5 MHz | 4.5 mm | 25-50 W | 25-50 ms | 0.5-1.5 J |
| P3 | 4.4 MHz | 4.5 mm | 25-60 W | 25-60 ms | 0.5-2.0 J |

The position of the marker specifies where a lesion will be placed on the tissue shown in the image. The computer 16 determines whether the operator has entered a command to begin ablation (step 70). Upon receiving a command to begin ablation, the computer sends an ablation control signal to the control circuitry 12, which in turn stimulates the ablation transducer 54 in applicator 36 to ablate the target volume 44 for the specified application period (step 72). The ultrasound radiation 42 is sufficient to produce a lesion of a desired volume within the target tissue volume 44 without damaging any surrounding tissue. The result of the ablation is an appropriately-sized lesion produced at the coordinates represented by the marker. In some embodiments, the result is a pattern of appropriately-sized lesions produced at the coordinates represented by the marker.

In some embodiments, in which the power and frequency of the ultrasound radiation 42 is adjusted electronically, the operator uses the same probe tip 38 even when the power and frequency specification changes. To change the power and frequency of the ultrasound radiation 42, the computer 16 sends the power and frequency specifications to the control circuitry 12, which in turn stimulates the transducers in the applicator 36 to produce ultrasonic radiation 42 having the specified power and frequency. In some embodiments, if a lesion pattern is specified at the computer 16, the computer 16 sends the pattern specifications to the control circuitry 12, which in turn stimulates multiple ablation transducers in the applicator 36 to direct the ultrasound radiation 42 such that the specified pattern of lesions is produced.

The ablation process 60 shown in FIG. 2 can also be used to ablate target volumes of SMAS tissue. Lesions produced in the SMAS layer induce shrinkage of the fibrous layers within the affected SMAS tissue. As the fibrous layers shrink, the skin attached to the SMAS layer is pulled tighter. The patterns and/or orientation of the lesions may be varied to impact the direction and amount by which the skin is pulled. In some embodiments, the pulling action induced by a particular pattern is affected by characteristics of the skin and underlying tissue layers. Examples of these characteristics include thickness and elasticity. The lesion patterns that are best suited to produce a desired pulling affect given a particular skin characteristic are determined from cadaver and clinical studies. Based on these results, an optimal lesion pattern is selected. Examples of lesion patterns include squares, triangles, polygons, grids, criss-cross patterns, and other patterns of straight lines. In some embodiments, the lesions patterns include circles, ovals, coils, and other patterns of curved lines. Lesions produced in SMAS or other connective tissues (e.g., periosteum) may be positioned to cause the connective tissues to release from the muscle tissue to which they are attached. For example, a non-invasive browlift could be performed by releasing SMAS or periosteum from muscles that pull the eyebrows downward. Releasing the SMAS or periosteum causes eyebrows to move upward because the frontalis muscles that pull the eyebrows upward are no longer opposed by the downward pulling muscles.

The ablation process 60 could also be used to reduce or remove unwanted fat from the face and other areas of the body.

Figure 3:
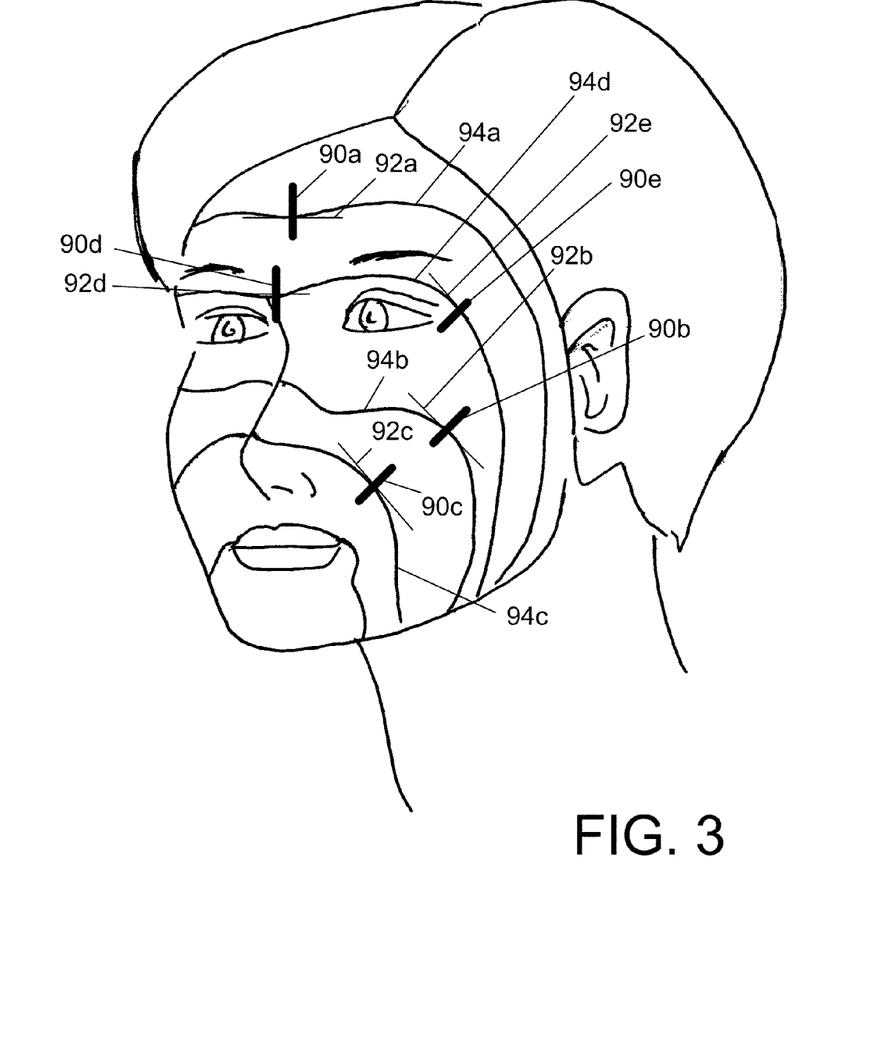
FIG. 3 shows exemplary lesion placements and orientations.

FIG. 3 shows exemplary orientations of lesions 90a, 90b, 90c, 90d, and 90e with respect to relaxed skin tension lines (RSTLs) 94a, 94b, 94c, and 94d. RSTLs 94a, 94b, 94c, and 94d are the natural skin lines and creases of the face and neck along which wrinkles and sagged skin tend to form. To tighten sagging skin and wrinkles, especially those formed along RSTLs 94a, 94b, 94c, and 94d, the lesions 90a, 90b, 90c, 90d, and 90e are produced in the SMAS and muscle tissues. The lesions 90a, 90b, 90c, 90d, and 90e are oriented approximately perpendicular to lines 92a, 92b, 92c, 92d, and 92e that are tangential to the points on the RSTLs 94a, 94b, 94c, 94d at which lesions are to be produced.

EXAMPLES

The feasibility and performance of the tissue ablation process (FIG. 2) using the ultrasound-delivery system (FIG. 1) were tested using experiments on porcine and human cadaver tissues. In the human cadaver studies, energy was varied over a given set of source conditions to see which energy levels would produce selective muscle heating.

Figure 4:
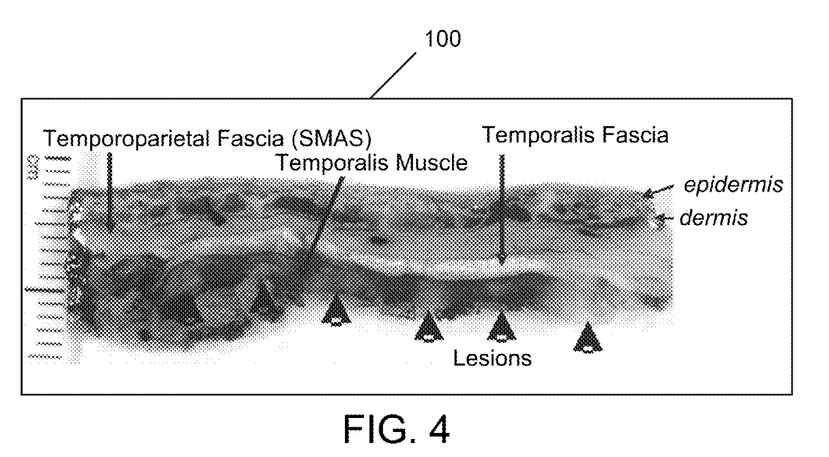
FIG. 4 shows an image of lesions produced on a temporalis muscle.

FIG. 4 shows a an image 100 of lesions produced on a temporalis (forehead) muscle of a human cadaver using ultrasound having a frequency of 4.4 MHz, a focal distance of 4.5 mm, a power of 80 W. The ultrasound was applied as a series of pulses, each applied over a duration of approximately 60 ms. In the image 100, the locations of the lesions are marked with black arrows. The volumes of the lesions were measured to be approximately 1 mm$^3$. The depths of the lesions from the surface of the skin ranged between approximately 5 to 6 mm. In the human studies that produced lesions within the dermis, the energy of the applied ultrasound ranged between approximately 0.5 to 2 Joules. In some of the studies, an energy of 1.2 J was optimal for producing lesions having a desired volume of 1 mm$^3$.

Figure 5:
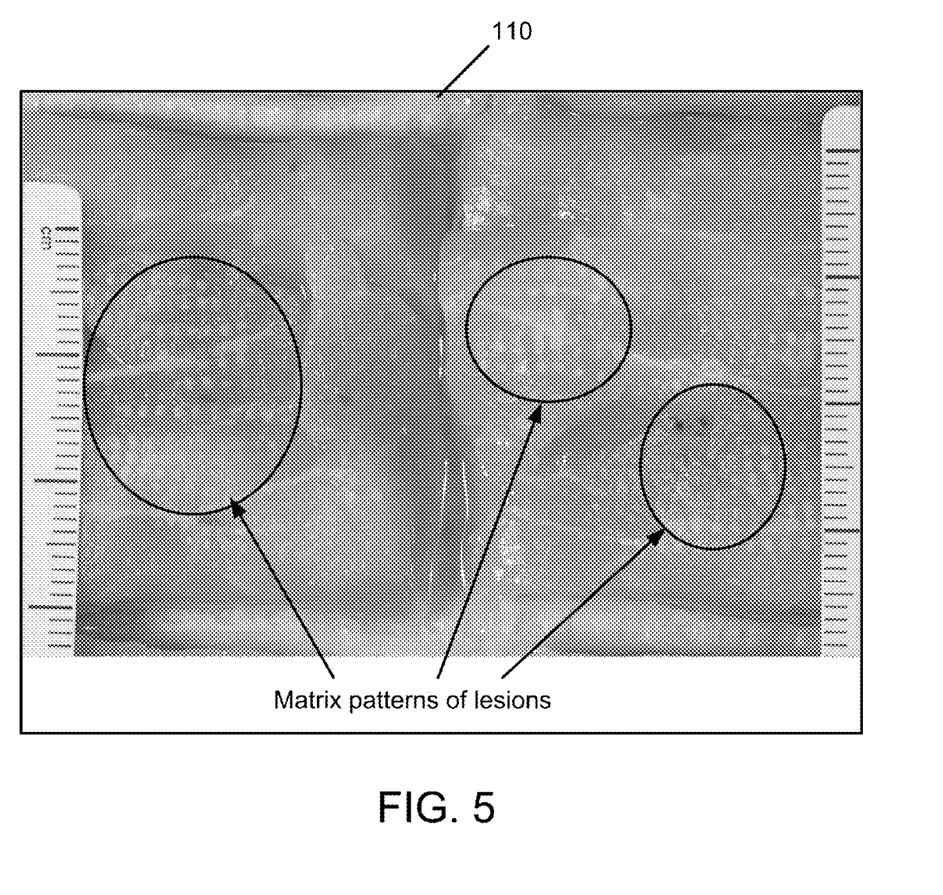
FIG. 5 shows an image of lesions produced on a porcine muscle.

FIG. 5 shows an image 110 of lesions produced on a cross-section of porcine muscle. The depths of the lesions beneath the surface of the skin are approximately 4 mm. The lesions shown in image 110 are arranged as three dimensional grid of approximately equally spaced lesions, referred to as "matrix pattern." The volumes of the lesions are approximately 1 mm$^3$ and the spacings between lesions are approximately 1 mm. The matrix pattern was formed by laying down successive rows of five lesions using an ultrasound applicator having focal distances of 4.5 and 7.5 mm. The lesions of each row were produced simultaneously. The density of the lesions shown in image 110 is approximately 125 lesions per cm$^3$.

The pattern of lesions was shown to affect (1) the degree and direction of pull in SMAS tissue and (2) the degree of paralysis in muscle tissue. Delivering a larger number of lesions per given surface area allow a "volumetric effect" and was shown to induce a greater collagen contraction in SMAS tissue. When placed a sufficient distance apart, the lesions contract toward each other. Lesions between approximately 1-2 mm$^3$ and spaced approximately 1-2 mm$^3$ away from each other in a matrix pattern provided a desired effect of SMAS tissue shrinkage and muscle paralysis. The experiments suggest that a matrix pattern of lesions delivered to the facial musculature would produce a greater paralysis of the muscles than other types of patters. The experiments also suggest that increasing the density of lesions within a volume increases the amount of tissue contraction within that volume.

The experiments described above demonstrate the feasibility of transcutaneously targeting and subsequently ablating muscle tissue without damaging the overlying skin tissue. Unlike some conventional methods that direct energy at the skin, the tissue ablation process (FIG. 2) enables energy to be focused at a depth selectively in tissue to induce a desired effect (e.g., SMAS tissue shrinkage and/or muscle paralysis).

A number of embodiments of the invention have been described. Nevertheless, it will be understood that various modifications may be made without departing from the spirit and scope of the invention. For example, the ultrasound delivery system 10 can be modified to deliver ablating radiation 42 and imaging radiation in the form of electromagnetic energy, e.g., radiofrequency (RF) energy, rather than ultrasound.

In some embodiments, a needle is used to deliver the ablative energy percutaneously to the target volume 44. The ablative energy may be in the form of electromagnetic radiation (e.g., radiofrequency) or ultrasound radiation or other modalities such as electrical current or laser energy. The needle is guided to the target volume 44 using ultrasound echo imaging as described above. The needle then delivers the ablative energy to the target volume 44 until a finite volume of tissue within the target volume coagulates and forms a lesion. In some embodiments, an array of needles carrying electricity is inserted through the skin and positioned within the target volume 44 of muscle. As current flows between needles, ohmic heating cauterizes the target volume 44 of muscle.

A needle, rather than ultrasound echo imaging, may be used to map the position of the target volume 44. In some embodiments, a needle inserted into the muscle 56 carries current to nearby muscle that is either touching the needle or located close (i.e., within approximately 1 to 2 mm depending on the amount of energy delivered) to the needle. The current stimulates activity in the muscle and nerve tissue. The computer 16 analyzes the activity in the muscle and nerve tissue and determines where the location of the needle relative to muscle and nerve tissue. As the needle moves, the computer 16 analyzes the muscle and nerve tissue activity and produces a map of the region that is traversed by the needle. The operator identifies the target volume 44 in the map and guides the needle to the target volume 44.

Accordingly, these and other embodiments are within the scope of the following claims.

What is claimed is:

1. A method for removing wrinkles in a subject's forehead, the method comprising:
   producing a map of a forehead muscle of the subject;
   using the map, locating a target volume of the forehead muscle, wherein the target volume is between about 2 mm and about 12 mm below an epidermal surface of the subject; and
   delivering energy to the target volume at a power, a frequency, and for a time selected such that the energy creates a pattern of lesions in the target volume, the pattern selected to achieve a desired degree of paralysis of the muscle, wherein each of the lesions in the pattern is confined within the target volume and the delivered energy does not significantly damage tissue surrounding the target volume.

2. The method of claim 1, further comprising selecting a characteristic of the lesion to paralyze the muscle.

3. The method of claim 2, wherein the characteristic comprises at least one of: a size, a shape, a depth below the epidermal surface, and a location relative to another lesion.

4. The method of claim 1, wherein delivering energy comprises selecting the energy to be ultrasound.

5. The method of claim 1, wherein delivering energy comprises selecting the energy to be radio frequency electromagnetic energy.

6. The method of claim 1, wherein the selected frequency is within a range of 4 to 8 MHz; and the selected power is within a range of 60 to 80 W.

7. The method of claim 1, wherein producing the map comprises acquiring an echo image of the muscle from echoes generated by reflections of ultrasound pulses directed towards the muscle.

8. The method of claim 1, further comprising selecting the pattern to be one of: a square, triangle, polygon, grid, crisscross pattern, circle, oval, and coil.

9. The method of claim 1, further comprising selecting the pattern to be a matrix of lesions spaced approximately equidistant from each other.

10. The method of claim 9, further comprising:
    selecting the lesions to be approximately 1 mm$^3$ in volume; and
    selecting spacings between the lesions to be approximately 1 mm.

11. The method of claim 1, wherein the forehead muscle includes at least one of a corrugator, a procerus, and a frontalis muscle.

12. The method of claim 1, wherein delivering the energy to the target volume further comprises focusing the energy into the target volume.

* * * * *